US007713297B2

(12) United States Patent
Alt (10) Patent No.: US 7,713,297 B2
(45) Date of Patent: May 11, 2010

(54) DRUG-RELEASING STENT WITH CERAMIC-CONTAINING LAYER

(75) Inventor: Eckhard Alt, Ottobrunn (DE)

(73) Assignee: Boston Scientific SciMed, Inc., Maple Grove, MN (US)

( * ) Notice: Subject to any disclaimer, the term of this patent is extended or adjusted under 35 U.S.C. 154(b) by 179 days.

(21) Appl. No.: 10/651,562

(22) Filed: Aug. 29, 2003

(65) Prior Publication Data

US 2004/0039438 A1   Feb. 26, 2004

(51) Int. Cl.
    *A61F 2/06* (2006.01)
(52) U.S. Cl. .................................. 623/1.39; 623/1.46
(58) Field of Classification Search ................ 623/1.15, 623/1.34, 1.39, 1.42, 1.43, 1.44, 1.46
    See application file for complete search history.

(56) References Cited

U.S. PATENT DOCUMENTS

| 3,758,396 A | 9/1973 | Vieth et al. |
| 3,910,819 A | 10/1975 | Rembaum et al. |
| 3,948,254 A | 4/1976 | Zaffaroni |

(Continued)

FOREIGN PATENT DOCUMENTS

| CA | 1283505 | 4/1991 |

(Continued)

OTHER PUBLICATIONS

"Cyclic voltammetry" - from Wikipedia, (http://en.wikipedia.org/wiki/Cyclic_voltammetry).

(Continued)

*Primary Examiner*—William H. Matthews
(74) *Attorney, Agent, or Firm*—Fish & Richardson P.C.

(57) ABSTRACT

A vascular or endoluminal stent is adapted to be implanted in a vessel, duct or tract of a human body to maintain an open lumen at the site of the implant. The sidewall of the open-ended tubular structure of the stent is a base layer of a metal biologically compatible with blood and tissue of the human body. An intermediate metal particle layer of substantial greater radiopacity overlies the base layer, with particles bonded to the base layer and to each other to leave interstices therebetween as a repository for retaining and dispensing drugs or other agents for time release therefrom after the stent is implanted, to assist the stent in maintaining the lumen open. The particles are composed primarily of a noble metal—an alloy of platinum-iridium. The sidewall has holes extending therethrough, and the particle layer resides along the outward facing and inward facing surfaces, and the edges of the through holes and open ends of the sidewall. The larger particles are bonded to surfaces of the sidewall and progressively smaller particles are bonded to those and to each other up to the outer portion of the particle layer. Exposed surfaces of the particle layer are coated with ceramic-like iridium oxide or titanium nitrate, as a biocompatible material to inhibit irritation of tissue at the inner lining of the vessel when the stent is implanted. One or more anti-thrombotic, anti-platelet, anti-inflammatory and/or anti-proliferative drugs are retained in the interstices, together with a biodegradable carrier for time release therefrom. In an alternative embodiment, the intermediate layer is solid and the biodegradable carrier and drugs or agents therein are applied to the surface of the ceramic-like coating. Gene transfer is alternatively used to control tissue proliferation.

23 Claims, 1 Drawing Sheet

U.S. PATENT DOCUMENTS

| | | | |
|---|---|---|---|
| 3,952,334 A | 4/1976 | Bokros et al. | |
| 3,993,072 A | 11/1976 | Zaffaroni | |
| 4,101,984 A | 7/1978 | MacGregor | |
| 4,143,661 A | 3/1979 | LaForge et al. | |
| 4,202,055 A | 5/1980 | Reiner et al. | |
| 4,237,559 A | 12/1980 | Borom | |
| 4,308,868 A | 1/1982 | Jhabvala | |
| 4,334,327 A | 6/1982 | Lyman et al. | |
| 4,401,546 A | 8/1983 | Nakamura et al. | |
| 4,585,652 A | 4/1986 | Miller et al. | |
| 4,655,771 A | 4/1987 | Wallsten | |
| 4,657,544 A | 4/1987 | Pinchuk | |
| 4,665,896 A | 5/1987 | LaForge et al. | |
| 4,705,502 A | 11/1987 | Patel | |
| 4,733,665 A | 3/1988 | Palmaz | |
| 4,784,659 A | 11/1988 | Fleckenstein et al. | |
| 4,800,882 A | 1/1989 | Gianturco | |
| 4,886,062 A | 12/1989 | Wiktor | |
| 4,954,126 A | 9/1990 | Wallsten | |
| 4,976,692 A | 12/1990 | Atad | |
| 4,994,071 A * | 2/1991 | MacGregor | 606/194 |
| 5,061,275 A | 10/1991 | Wallsten et al. | |
| 5,061,914 A | 10/1991 | Busch et al. | |
| 5,073,365 A | 12/1991 | Katz et al. | |
| 5,091,205 A | 2/1992 | Fan | |
| 5,102,403 A | 4/1992 | Alt | |
| 5,120,322 A | 6/1992 | Davis et al. | |
| 5,125,971 A | 6/1992 | Nonami et al. | |
| 5,147,370 A | 9/1992 | McNamara et al. | |
| 5,163,958 A | 11/1992 | Pinchuk | |
| 5,195,969 A | 3/1993 | Wang et al. | |
| 5,205,921 A | 4/1993 | Shirkanzadeh | |
| 5,236,413 A | 8/1993 | Feiring | |
| 5,270,086 A | 12/1993 | Hamlin | |
| 5,279,292 A | 1/1994 | Baumann et al. | |
| 5,290,585 A | 3/1994 | Elton | |
| 5,302,414 A | 4/1994 | Alkhimov et al. | |
| 5,304,121 A | 4/1994 | Sahatjian | |
| 5,314,453 A | 5/1994 | Jeutter | |
| 5,322,520 A | 6/1994 | Milder | |
| 5,348,553 A | 9/1994 | Whitney | |
| 5,366,504 A | 11/1994 | Andersen et al. | |
| 5,380,298 A | 1/1995 | Zabetakis et al. | |
| 5,383,935 A | 1/1995 | Shirkhanzadeh | |
| 5,397,307 A | 3/1995 | Goodin | |
| 5,405,367 A | 4/1995 | Schulman et al. | |
| 5,439,446 A | 8/1995 | Barry | |
| 5,443,496 A | 8/1995 | Schwartz et al. | |
| 5,449,373 A | 9/1995 | Pinchasik et al. | |
| 5,449,382 A | 9/1995 | Dayton | |
| 5,464,450 A | 11/1995 | Buscemi et al. | |
| 5,464,650 A | 11/1995 | Berg et al. | |
| 5,474,797 A * | 12/1995 | Sioshansi et al. | 427/2.24 |
| 5,500,013 A | 3/1996 | Buscemi et al. | |
| 5,527,337 A | 6/1996 | Stack et al. | |
| 5,551,954 A | 9/1996 | Buscemi et al. | |
| 5,578,075 A | 11/1996 | Dayton | |
| 5,587,507 A | 12/1996 | Kohn et al. | |
| 5,591,224 A | 1/1997 | Schwartz et al. | |
| 5,603,556 A | 2/1997 | Klink | |
| 5,605,696 A | 2/1997 | Eury et al. | |
| 5,607,463 A | 3/1997 | Schwartz et al. | |
| 5,609,629 A | 3/1997 | Fearnot et al. | |
| 5,624,411 A | 4/1997 | Tuch | |
| 5,649,951 A | 7/1997 | Davidson | |
| 5,672,242 A | 9/1997 | Jen | |
| 5,674,192 A | 10/1997 | Sahatjian et al. | |
| 5,674,242 A | 10/1997 | Phan et al. | |
| 5,679,440 A | 10/1997 | Kubota | |
| 5,690,670 A | 11/1997 | Davidson | |
| 5,693,085 A | 12/1997 | Buirge et al. | |
| 5,693,928 A | 12/1997 | Egitto et al. | |
| 5,824,077 A | 10/1998 | Mayer et al. | |
| 5,843,089 A | 12/1998 | Sahatjian et al. | |
| 5,843,172 A * | 12/1998 | Yan | 623/1.42 |
| 5,858,556 A | 1/1999 | Eckert et al. | |
| 5,873,904 A | 2/1999 | Ragheb et al. | |
| 6,174,329 B1 * | 1/2001 | Callol et al. | 623/1.34 |

FOREIGN PATENT DOCUMENTS

| | | |
|---|---|---|
| CA | 2178541 | 12/1996 |
| DE | 3608158 | 9/1987 |
| DK | 127987 | 9/1987 |
| EP | 0129147 | 1/1990 |
| EP | 07134721 | 10/1996 |
| EP | 0850604 | 12/1997 |
| JP | 3673973 | 2/1996 |
| JP | 3249383 | 10/1996 |
| WO | WO93/06792 | 4/1993 |
| WO | WO93/07934 | 4/1993 |
| WO | WO93/16656 | 9/1993 |
| WO | WO94/16646 | 8/1994 |
| WO | WO95/03083 | 2/1995 |
| WO | WO96/04952 | 2/1996 |
| WO | WO96/09086 | 3/1996 |
| WO | WO96/32907 | 10/1996 |
| WO | WO97/041916 | 11/1997 |

OTHER PUBLICATIONS

"Electrophoretic deposition" - from Wikipedia, (http://en.wikipedia.org/wiki/electrophoretic_deposition).

"Ultraviolet-Ozone Surface Treatment," Three Bond Technical News #17, pp. 1-10, Issued Mar. 20, 1987, (http://www.threebond.co.jp/en/technical/technicalnews/pdf/tech17.pdf).

Ansell et al., "X-Ray Photoelectron Spectroscopic Studies of Tin Electrodes after Polarization in Sodium Hydroxide Solution," Journal of Electrochemical Society: Electrochemical Science and Technology, vol. 124, No. 9, pp. 1360-1364, Sep. 1977.

Atanasoska et al., "XPS Studies on Conducting Polymers: Polypyrrole Films Doped with Perchlorate and Polymeric Anions," Chemistry Materials vol. 4, pp. 988-994, (1992).

Brukner et al., "Metal plasma immersion ion implantation and deposition (MPIIID): chromium on magnesium," Surface and Coatings Technology vol. 103-104, pp. 227-230, (1998).

Chandra et al., "Biodegradable Polymers," Progress in Polymer Science, vol. 23, pp. 1273-1335, (1998).

Cho et al., "Preparation and Characterization of Iridium Oxide Thin Films Grown by DC Reactive Sputtering," Japanese Journal of Applied Physics, vol. 36, Part 1, No. 3B, pp. 1722-1727, Mar. 1997.

Clark, "Micropatterning Cell Adhesiveness", Immobilized Biomolecules in Analysis, Oxford University Press, pp. 95-111, (1998).

Comparison of Iridiumoxide Coated Stent with Paclitaxel-Eluting Stent and a Bare Metal Stent in Patients With Coronary Artery Disease, Abstract.

Curtis et al., "New depths in cell behaviour: Reactions of cells to nanotopography," Biochemical Society Symposium, No. 65, pp. 15-26 (1997).

Curtis et al., "Topographical Controls of Cells," Biomaterials, vol. 18, pp. 1573-1583, (1997).

DTI Technology Group: Materials-Coating, "Kinetic spray coating method," www.delphi.com.

Glocker et al., "Recent developments in inverted cylindrical magnetron sputtering," PowerPoint presentation.

Green et al., "XPS Characterisation of Surface Modified Ni-Ti Shape Memory Alloy," Materials Science and Engineering, vol. A224, pp. 21-26, (1997).

Haberland et al., "Fling of micron-sized contact holes with copper by energetic cluster impact," Journal of Vacuum Science Technology A, vol. 12, No. 5, pp. 2925-2930, Sep./Oct. 1994.

Helmus et al. "Surface Analysis of a Series of Copolymers of $_L$-Glutamic Acid and $_L$-Leucine," Journal of Colloid and Interface Science, vol. 89, No. 2, pp. 567-570, (1982).

Helmus et al., "Plasma Interaction on Block Copolymers as Determined by Platelet Adhesion," Biomaterials: Interfacial Phenomena and Applications: Chapter 7, pp. 80-93, (1981).

Helmus et al., "The Effect of Surface Charge on Arterial Thrombosis," Journal of Biomedical Materials Research, vol. 18, pp. 165-183, (1984).

Hüppauff et al., "Valency and Structure of Iridium in Anodic Iridium Oxide Films," Journal of Electrochemical Society, vol. 140, No. 3, pp. 598-602, Mar. 1993.

HyFraSurf-Advanced Surface Technology for Superior Electrode Performance, Sulzer Innotec.

Kesler etal., "Enhanced Strength of Endothelial Attachment on Polyester Elastomer and Polytetrafluoroethylene graft Surfaces with Fibronectin Substrate," Journal of Vascular Surgery, vol. 3, No. 1, pp. 58-64, (1986).

Kesting, "Synthetic Polymeric Membranes - A Structural Perspective", Chapters 6-7, pp. 225-286.

Kim et al., "Hollow Silica Spheres of Controlled Size and Porosity by Sol-Gel Processing," Journal of Americal Ceramic Society, vol. 74, Nol. 8, pp. 1987-1992, (1991).

Kopanski et al., "Scanning Kelvin Force Microscopy for Characterizing Nanostructures in Atmosphere," National Institute of Standards and Technology: Semiconductor Electronics Division.

Kötz et al., "XPS Studies of Oxygen Evolution on Ru and $RuO_2$ Anodes," Journal of Electrochemical Society: Electrochemical Science and Technology, pp. 825-829, Apr. 1983.

Martin, "Pulsed Laser Deposition and Plasma Plume Investigations," Andor Technology, Ltd.

Mauritz Group Homepage, "Sol-Gel Chemistry and Technology," htty://www.psrc.usin.edu/mauritz/solgel.html.

Nanoparticle coatings: Application note, "Antimicrobialcoatings," MANTIS Deposition Ltd.

Park et al., "Novel Phenylethynyl Imide Silanes as Coupling Agents for Titanium Alloy," National Research Council, Composites and Polymers Branch.

Peng et al., "Role of polymers in improving the results of stenting in coronary arteries," . Biomaterials, vol. 17, No. 7, pp. 658-694 (1996).

Perlman et al., "Evidence for rapid onset of apoptosis in medial smooth muscle cells after balloon injury," Circulation, vol. 95, No. 4, pp. 981-987, Feb. 18, 1997.

Prokopowicz et al., "Utilization of Standards Generated in the Process of Thermal Decomposition Chemically Modified Silica Gel or a Single Point Calibration of a GC/FID System," Talanta, vol. 44, pp. 1551-1561, (1997).

Qiang et al., "Hard coatings (TiN, $Ti_xAl_{1-x}N$) deposited at room temperature by energetic cluster impact," Surface and Coatings Technology, 100-101, pp. 27-32, (1998).

Rees et al., "Glycoproteins in the Recognition of Substratum by Cultured Fibroblasts," Symposia of the Society for Experimental Biology: Cell-Cell Recognition, No. 32, pp. 241-260.

Rosen et al., "Fibrous Capsule Formation and Fibroblast Interactions at Charged Hydrogel Interfaces," Hydrogels or Medical and Related Applications, Chapter 24, pp. 329-343.

Sawyer et al., "The Role of Electrochemical Surface Properties in Thrombosis at Vascular Interfaces: Cumulative Experience of Studies in Animals and Man," Bulletin of the New York Academy of Medicine, Second Series, vol. 48, No. 2, pp. 235-256, (1972).

Sawyer, "Electrode-Biologic Tissue Interreactions at Interfaces - A Review;" Biomat. Med. Dev. Art. Org., 12(3-4), pp. 161-196 (1984).

Schetsky, "Shape Memory Alloys", Encyclopedia of Chemical Technology (3rd ed.), John Wiley & Sons, vol. 20, pp. 726-736, (1982).

Scheuermann, "PIII experiments at Axyntec," PowerPoint presentaction.

Shevchenko et al., "Porous Surface of NiTi Alloy Produced by Plasma Ion Implantation," Institute of Ion Beam Physics and Materials Research.

Siegfried et al., "Reactive Cylindrical Magnatron Deposition of Titanium Nitride and Zirconium Nitride Films," Society of Vacuum Coaters, 39th Annual Technical Conference Proceedings, pp. 97-101, (1996).

Silber et al., "A new stainless-steel-free stent with a potential of artifact free magnetic resonance compatibility: first clinical experience (Ein neuer Edelstahl-freier Stent mit Potential zur artefaktfreien MR-Kompatibilität: Erste klinische Erfahrungen)," German Society for Cardiology-Heart and Cardiovascular Research (Deutche Gesellschaft fur Kardiologie-Herz and Kreislaufforschung).

The reactive DC-Magnetron Sputtering Process.

Vidal et al., "Electropolymerization of pyrrole and immobilization of glucose oxidase in a flow system: influence of the operating conditions on analytical performance," Biosensors & Bioelectronics, vol. 13, No. 3-4, pp. 371-382, (1998).

Vukovié et al., "Anodic stability and electrochromism of electrodeposited ruthenium-iridium coatings on titanium," Journal of Electroanalytical Chemisty, vol. 330, pp. 663-673 (1992).

Wesolowski et al., "Surface Charge and Ion Adsorption on Metal Oxides to 290°C," Division of Chemical Sciences, Geosciences, and Biosciences, Office of Basic Energy Sciences, U.S. Department of Energy.

* cited by examiner

DRUG-RELEASING STENT WITH CERAMIC-CONTAINING LAYER

CLAIM OF PRIORITY

This application claims priority under 35 USC §120 to U.S. patent application Ser. No. 09/740,570, filed on Dec. 15, 2000 and now abandoned, which is a continuation of U.S. patent application Ser. No. 09/059,053 filed on Apr. 1, 1998 and now abandoned, the entire contents of which are hereby incorporated by reference.

BACKGROUND OF THE INVENTION

The present invention relates generally to stents which are implantable or deployable in a vascular or endoluminal location within the body of a patient to maintain the lumen open at the implant site, and more particularly to improvements in stent coatings.

Stents are expandable prostheses employed to maintain narrow vascular and endoluminal ducts or tracts of the human body open and unoccluded, such as a portion of the lumen of a coronary artery after dilatation of the artery by balloon angioplasty, for example. In the exemplary case of an occluded coronary artery, the original blockage typically arises from a buildup of fatty deposits or plaque on the inner lining of the vessel. The balloon angioplasty procedure is used to compress the deposits against the inner lining of the vessel, or virtually entire removal may be achieved using other types of angioplasty such as laser or rotational cutting. A different mechanism, however, may cause a new blockage after the angioplasty procedure is performed. The blood vessel wall is subjected to trauma by the balloon, laser or rotating knife, as the case may be, which results in intimal hyperplasia, i.e., a rapid proliferation of smooth muscle cells in the affected region of the wall, to cause restenosis and re-occlusion of the vessel lumen in a significant percentage of angioplasty patients within a period of from three to six months following the initial procedure.

To avoid this re-occlusion and to maintain the lumen of the vessel open, it is now customary procedure to install a stent at the site in the vessel where the angioplasty was performed. The stent is deployed by radial expansion under pressure exerted, for example, by active inflation of a balloon of a balloon catheter on which the stent is mounted, or in some instances by passive spring characteristics of a pre-formed elastic stent, to engage the inner lining or inwardly facing surface of the vessel wall with sufficient resilience to allow some contraction but also with sufficient stiffness to resist to a great degree the natural recoil of the vessel wall that follows its expansion.

The stent itself, however, offers a surface that can promote thrombus formation as blood flows through the vessel. This can result in an acute blockage, which, in a coronary artery, is sufficient to produce an infarction. The thrombosis and clotting can be reduced or even eliminated by localized application of appropriate drugs in a biodegradable formulation, which act for only a period of time sufficient to stave off the thrombus reaction to the presence of the stent in the bloodstream. Some difficulty is encountered in providing a stent surface which is suitable for retention of the necessary drug(s) to achieve those purposes.

A similar situation is encountered at the outward facing surface of the stent that contacts and engages the inner lining of the vessel, duct or tract, where tissue irritation can exacerbate fibrosis of the vessel wall and restenosis in the region of the irritation. Here, also, it would be desirable to provide the stent with the capability to provide a timed release of suitable drug(s) from a biodegradable carrier on or in the affected stent surface, to reduce the occurrence of fibrosis and hyperplasia at the portion(s) of the vessel wall contacted by the stent.

An additional need encountered for stent usage in the human body include a capability to clearly visualize the stent as it is being implanted at the preselected site in the body, as by advancement on a stent delivery system through a portion of the patient's vascular system and into a coronary artery, and after the stent is implanted, for purposes of its examination from time to time at the implant site.

Among the most important features of a suitable stent are the following. The device should be flexible, and yet possess sufficient mechanical strength to resist vessel recoil. It should demonstrate a high rate of successful interventional placement, be highly visible on x-ray fluoroscopy, be very thin to minimize obstruction by its mere presence in the lumen intended to be dilated and held open, and not be an agent which promotes a re-narrowing or re-occlusion of the vessel or duct lumen in which it is implanted. Stent design, of course, can play a major role in influencing the aforementioned features, but also significant is the material(s) of which the stent is composed, with respect to visibility, flexibility, and recoil-resistant characteristics of the stent, as well as its surface characteristics that affect capability of the stent to prevent or inhibit thrombus formation and restenosis in a blood vessel in which the stent is implanted. Current stents have not proved to be capable of fulfilling all of these requirements.

Therefore, it is a principal aim of the present invention to provide a stent which has a composition that offers an enhanced capability to fulfill these important requirements.

SUMMARY OF THE INVENTION

A stent is adapted for deployment in a blood vessel of a human body to maintain the lumen of the vessel open for adequate flow of blood therethrough in the region in which the stent is deployed. The stent has the basic form of an open-ended tubular element with openings through a side thereof, which is adapted to be expanded from a first outside diameter, which is sufficiently small to allow the stent and its delivery system to traverse the vascular system of the human body to reach a site in the blood vessel at which the stent is to be deployed, to a second outside diameter sufficiently large to engage the inner lining of the vessel for retention at the site.

According to a preferred embodiment of the invention, the tubular element or sidewall of the stent includes a first solid layer or thickness of a biocompatible metal, and a second porous layer or thickness which is composed of spherically-shaped metal particles bonded together to leave spaces between the particles. The metal particles are composed at least in part of a noble metal, and specifically, of a platinum-iridium alloy. The spaces between the particles advantageously provide a repository for drugs to assist in maintaining the lumen of the vessel open. The second thickness overlies the first thickness in tightly adherent relation thereto, and has a radiopacity which substantially exceeds that of the first thickness, to provide a highly visible view of the stent by x-ray fluoroscopy during its advancement and deployment in the blood vessel, and thereafter whenever the stent is to be examined in place.

The stent includes at least one drug selected from a group consisting of anti-thrombotic, anti-platelet, anti-inflammatory and anti-proliferative drugs, residing in the repository. A biodegradable carrier may be used to retain the drugs for timed release thereof from the repository when the stent is deployed at the selected implant site in the blood vessel. Alternatively, the mere spacing of the metal particles may advantageously provide a timed release of the drugs from the repository. Preferably, for that purpose the particles, which are sized in a range of diameters, are located with the larger diameter sizes adjacent and bonded to the surface of the first thickness and with those and progressively smaller diameter sizes bonded together up to the outermost region of the second thickness. In either event, the anti-platelet and/or anti-thrombotic drugs are preferably infused into the porous layer repository, i.e., into the spaces or interstices between the particles, existing at the inward facing surface (and if desired, at directly adjacent edges of the openings) of the stent to inhibit clogging of the lumen as a result of interaction between the stent itself and the blood flow therethrough. Similarly, the anti-inflammatory and/or anti-proliferative drugs are preferably infused into the repository existing at the outward facing surface (and if desired, at directly adjacent edges of the openings) of the stent to inhibit restenosis as a result of fibrosis or proliferation of tissue from trauma to the inner lining of the vessel arising from contact with the stent.

According to another important feature of the invention, a third layer or thickness of a ceramic-like material—specifically, either iridium oxide or titanium nitrate—is applied as a coating overlying exposed surfaces of the metal particles in tightly adherent relation to the second thickness at those surfaces, without filling or blocking the spaces between the particles, so that the repository for drugs originally formed in the second thickness remains available. Consequently, the desired drugs may be infused into the spaces between particles, in preferential locations as noted above, for retention and dispensing in the same manner as if the third thickness had not been applied. Additionally, the ceramic-like material is resistant to tissue irritation to further avoid such traumatic response during contact of the stent with the inner lining of the vessel at the site.

In a method of fabricating such a multi-layer vascular or endoluminal stent, a porous layer of substantially spherical metal particles is applied atop surfaces of a base metal of the stent, the metal particles at the base metal surfaces being bonded thereto and the metal particles throughout the porous layer being bonded together, with voids therebetween forming a reservoir for retention and dispensing of drugs from the stent when deployed in its vascular or endoluminal location. The metal particles exhibit a radiopacity that substantially exceeds the radiopacity of the base metal for high visibility viewing of the stent by fluoroscopy when advanced and deployed in the body. After applying the porous layer, the exposed surfaces of the metal particles are coated with ceramic-like material consisting of iridium oxide or titanium nitrate while leaving the voids between the particles unblocked and substantially intact so that the reservoir remains available for infusing drugs therein.

The base metal may, for example, be 316L stainless steel, chromium, nickel, titanium, or iridium, or nitinol which is a shape memory nickel-titanium alloy, nominally of 70 micrometers or microns (μm) thickness. The metal particles of platinum-iridium alloy preferably have diameters ranging from about 50 to 500 nanometers, and the porous layer is applied atop the base metal to a thickness in a range from approximately 4 to 8 microns. The iridium oxide or titanium nitrate is coated on surfaces of the metal particles to a thickness in a range from approximately 50 to 500 nanometers. Thereafter, following steps of rinsing, cleaning and drying, the desired drugs or other selected agents are infused into the reservoir provided by the voids or interstices between particles of the porous layer. Timed release of the drugs may be achieved by incorporating them in a biodegradable carrier.

Gene transfer may alternatively be used to inhibit proliferation of smooth muscle cells, to prevent restenosis that could block the lumen of the vessel in which the stent is deployed. In this technique, a viral vector transfers at least part of the genetic information of interest to the target cell. A gene transfer agent constituting the viral vector or virus is incorporated in a biodegradable carrier, or microspheres or liposomes as the viral vector are contained in solution, and the combination is infused into the reservoir of the multi-layer stent from which it is released in a substantially programmed manner to effect the gene transfer.

As will be recognized from considering the detailed description below, a highly important aim of the invention resides in providing a basic structure of a stent which includes three fundamental layers, a first underlying layer constituting a base metal that functions to provide mechanical strength and flexibility, a second intermediate layer that functions to provide high fluoroscopic visibility—preferably a noble metal layer, and most preferably a principally platinum layer in which platinum is in an alloy with a small percentage (about 2%) of iridium—, and a top layer of particularly beneficial biocompatible material—preferably iridium oxide or titanium nitrate. Although the preferred embodiment utilizes a porous intermediate layer, and a remaining porous structure even after formation of the final biocompatible layer, in its most fundamental character the invention contemplates the use of a completely solid intermediate layer to provide the high visibility property and a highly suitable surface for strong bonding of the final coating. The latter itself offers a surface for attachment of the drug/agent-containing carrier.

BRIEF DESCRIPTION OF THE DRAWINGS

The above and still further aims, objects, features, aspects and attendant advantages of the present invention will be better understood from the detailed description below of the best mode presently contemplated of practicing the invention, with reference to the accompanying drawings, in which.

DETAILED DESCRIPTION OF A PREFERRED EMBODIMENT AND METHOD

Figure 1:
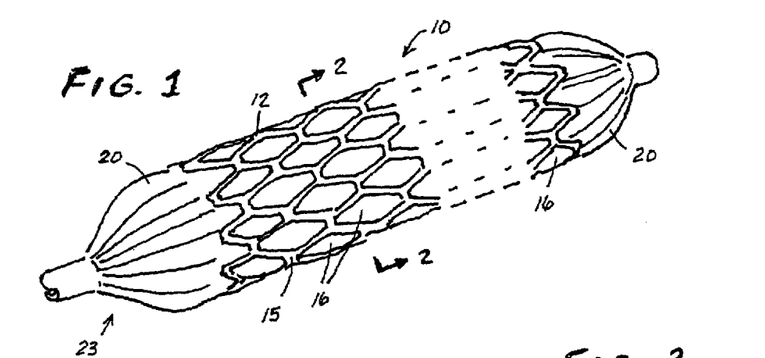
FIG. 1 is a partial perspective view of a basic form of vascular or endoluminal stent, incorporating a multi-layer structure according to the invention.
Figure 2:
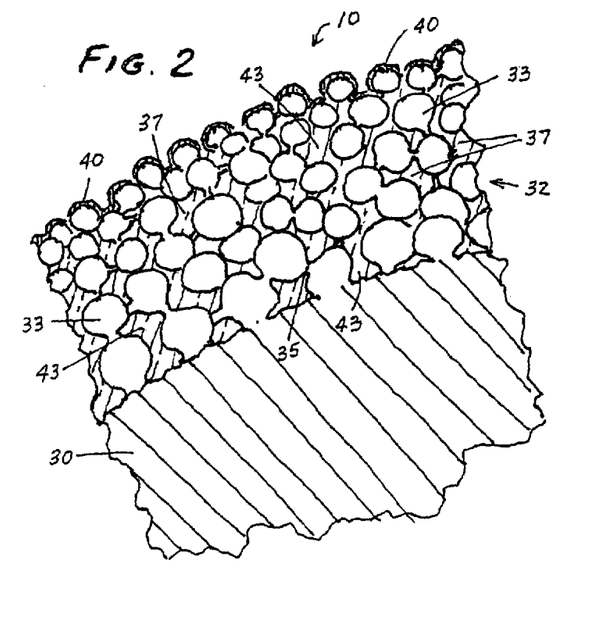
FIG. 2 is an exaggerated fragmentary cross-sectional detailed view of a portion of the multi-layer structure of the stent of FIG. 1, through the line 2-2 thereof.

In FIGS. 1 and 2 (the drawings are not intended to be to scale), a stent 10 may be of generally conventional configuration, with cylindrical structure having open ends, and of any known type such as the Palmaz-Schatz zig-zag tube type shown, or a mesh type, for example. The material of which the metal member 12 of the stent is composed, i.e., the wire or the solid tube, may be of any conventional and suitable type, such as medical grade 316L stainless steel, chromium, nickel, titanium, iridium or nitinol, for example, which is biologically compatible (biocompatible) with the fluids and tissue of the human body. In any event, the sidewall 15 of member 12 is provided with a multiplicity of openings 16 that extend entirely through the wall. For the mesh type stent, the openings are formed as a natural part of the formation of the mesh itself. If the stent is a helical spring-type of structure, the openings are simply the continuous winding space between the coils. For a solid tube type of starting member, openings may be cut in any conventional manner, such as by use of a cutting laser beam operating according to a computer-generated pattern. In the latter instance, care must be exercised to prevent the far side (relative to the position of the laser) of the tube from being cut at the same time that the near side cutting pattern is being produced.

The openings 16 are sized in a conventional manner to assure that body fluids (including blood, in the case of a vascular stent) can contact much of the tissue of the inner lining of the wall of a vessel, duct or tract of the human body in which the stent is to be implanted. For vascular stents, it is also important that side branches of vessels should remain open to the main branch of a vessel in which the stent is deployed. Considerations of stent expansion in a relatively symmetrical manner, and the presence of sufficient thickness of metal to provide enough rigidity to resist collapse as the vessel wall exerts its inward pressure during natural recoil when the stent is fully deployed, also play a significant role in determining the size and number of the sidewall openings, as well as the thickness and final configuration of the member 12 itself.

For implantation in a coronary artery, for example, the production diameter (outer diameter) of the stent 10 may be in a range from about 1.5 millimeters (mm) to 2.0 mm. In any event, the production diameter (or subsequent compressed diameter) constitutes a first diameter which is sufficiently small to allow the stent to be inserted into the vessel, duct or tract of the body in which it is being used, and to be advanced to the site at which it is to be deployed. At that point, the stent is deployed by inflation of the balloon on which it is mounted to radially expand the diameter to a second diameter which is at least slightly larger than the diameter of the lumen of the vessel, duct or tract at that point. In FIG. 1, the stent 10 is illustrated as being partially expanded on its balloon catheter, for the sake of clarity. It is common practice to pre-mount a stent on a balloon 20 of a balloon catheter 23 (partially shown in the Figure) of the stent delivery system, and to supply the combination in a sterile package for convenience of ready use by the implanting physician. Alternatively, the stent could be mounted on the balloon by the physician at the time the procedure is to be performed. If the stent is to be deployed by passive spring characteristics as in the case of a pre-formed elastic stent, the delivery system need not include a balloon.

Again using coronary artery implantation as an example, the mounted stent is inserted into the patient's vascular system (not shown) at an appropriate location, and is then advanced on the balloon catheter to the selected site. The path of the stent to the site of deployment as well as identification of the target site in the coronary artery are viewed and determined by fluoroscopy. When properly located at the target site, the balloon 20 is inflated by introducing a fluid through an inflation lumen of the catheter to radially expand the stent diameter to an extent that the stent will engage and exert at least slight pressure on the inner lining of the vessel wall. When the stent is fully deployed, the balloon is deflated and the catheter 23 is withdrawn from the patient's vascular system and body. The stent 10 should possess sufficient rigidity in the fully deployed expanded state to prevent it from collapsing under the radially directed inward pressure exerted by the artery wall from natural recoil thereof as the balloon is deflated.

When crimped onto the mounting balloon, the coronary artery stent outer diameter will typically lie in a range from about 0.9 to about 1.2 mm, with an inner diameter in a range from about 0.6 to about 0.7 mm. The inner diameter of the stent when fully deployed to the expanded diameter at the target site will typically lie in a range from about 2.5 to about 6.0 mm. The final deployed diameter should be a size which will assure that the stent is retained in place, firmly engaged with the inner lining of the artery wall.

For other vascular sites such as the renal artery, the carotid or femoral artery, or the ductus hepaticus in the liver, a diameter of approximately 4.0 to 8.0 mm is appropriate. This stent size range is produced from tubing of one of the aforementioned core metal materials, typically 316L stainless steel, of 3.2 mm outside diameter and arranged and adapted to be expanded (opened) to a larger outside diameter by cutting a predetermined pattern of openings through the sidewall of the stent. For applications in the bronchial location or in the vascular iliac location, a principal size range of from 8.0 to 12.0 mm outside diameter, fully opened, is desired. For esophageal applications in patients with malignant narrowing of the esophagus lumen, a range of diameter sizes from about 12.0 to 18.0 mm is adequate.

A stent 10 fabricated according to the present invention is composed of three different primary or fundamental layers as shown in the greatly exaggerated fragmentary cross-sectional view of FIG. 2, taken through the line 2-2 of FIG. 1. By "primary" and "fundamental", as used here, it is meant and intended that although the stent may have additional layers, coatings or films, the three layers to be described below are essential to the favorable characteristics enjoyed by the stent.

The base layer 30 of the tubular member 12 of stent 10 is a biocompatible metal or an alloy of metals which has been or can be demonstrated to be suitable for implantation in the human body. Each of the other layers of the multi-layer structure of the stent is also biocompatible but that feature is not necessarily its primary characteristic, as well be understood from the description below. Focusing on the base layer or core material thickness 30 of the stent, materials such as 316L stainless steel, or nickel-titanium alloy known as nitinol which has a shape memory property, among others, are popular in medical implants and possess favorable characteristics of elasticity, mechanical strength and fatigue. The mechanical strength must be adequate to resist recoil of the vessel wall and to provide a scaffold that maintains an adequate lumen opening for the vessel being stented. Stent deployment may be achieved by active balloon inflation, or by passive spring opening attributable to pre-formed elasticity of the stent base material. These results are typically achievable with very thin-walled stents, in a range from 60 to 80 micrometers or microns ($\mu$m) thick. However, the customary materials and material thicknesses are inadequate for sufficient visibility under fluoroscopic x-ray implantation or examination. In practice, this means that identifying the stent for deployment at the precise target site might be difficult, especially if the stent delivery system (e.g., a balloon catheter such as 23 in FIG. 1, in the case of active deployment) were not provided with radiopaque markers, and, that after implantation, greater difficulty may be encountered in attempting to locate the exact site of the stent for periodic examination, the advantage of the markers associated with the stent delivery system having been lost when the latter was withdrawn.

The atomic number (Z) of the base material may be about 28, in the case of medical grade stainless steel or nitinol, compared to Z=7.2 for the human body. To increase the visibility of a stent composed of such material under x-ray fluoroscopy, it is common practice to fabricate the stent tube to have a thickness of about 150 $\mu$m, which, however, results in an undesirable loss of lumen diameter of the vessel when the stent is implanted therein. Reducing the thickness of the stent by about half, to 75 μm, would result in a gain in lumen diameter of 150 μm (2×75 μm), or about 5% of the total lumen of a 3 millimeter (mm) vessel such as a coronary artery. Since the primary function of the stent is to maintain an unobstructed lumen in the vessel in which it is implanted, it is desirable, to the extent practicable, to avoid obstruction attributable to the mere thickness of the stent itself. Also, in general, the stiffness of a stent increases directly with the thickness of the material of which it is composed. Stent stiffness increases the order of difficulty of implanting the stent, which is another reason for finding ways to reduce thickness without seriously affecting mechanical strength and radiopacity of the stent.

In fabricating the stent 10, the base material 30 such as 316L stainless steel is formed into an open-ended tubular structure of approximately 70 μm thickness, for example, and of selected appropriate length. Openings are cut (in the case of a tubular member with a solid wall, in contrast to a mesh or spring wound type) in a predetermined pattern through its sidewall, as by laser cutting, for example. This allows the stent diameter to be expanded (opened, e.g., during deployment) from a selected production diameter which will depend on the inner diameter of the vessel or duct in which the stent is to be inserted and advanced to a selected site of implantation. After openings are provide in the sidewall of the tubular member, it is subjected to customary cleaning and polishing steps. All exposed surfaces of the stent, including the outward and inward facing surfaces, the edges of the through holes in the sidewall, and the ends of the sidewall, should be left at least slightly roughened, as by incomplete electro-polishing or by abrasion or by acid washing, or the like, to enhance adhesion of the next layer. Similar steps are followed if a shape memory or spring memory material is used, such as nitinol, although the stent itself in such a case might instead have a helical rather than a tubular configuration, which would eliminate the need for additional openings through a sidewall.

The next layer, which is to be applied atop the base metal layer 30, is intended to serve multiple purposes. In the preferred embodiment, this second, middle or intermediate layer 32 (again, these terms being used without limitation of the overall stent to only three layers or an absence of intervening layers) is preferably composed of a multiplicity of microspherical particles, or microspheres 33, of suitable metal or alloy, ranging in size (diameter) from about 50 to 500 nanometers (nm) and applied to form a layer thickness in a range from about 4 to about 8 μm, preferably nominally about 5 μm, atop the exposed surfaces of the sidewall constituted by base layer 30. The microspheres are built up on the surface of the tube in a manner such that the bottom or lowermost portion of the layer consists of microspheres adherent to the tube surface, and intervening portions up to the top or uppermost portion of this layer consist of microspheres connected or bonded (adherent) to one or more adjacent microspheres at points of tangency or near tangency (e.g., 35) therebetween. This configuration is such that voids or open spaces 37 are present throughout the layer, as interstices between adjacent microspheres. Thus, the intermediate layer may be characterized as being porous, and this is important for a purpose which will be discussed in detail presently.

To render the stent more radiopaque despite the relative thinness of the base layer (here, the tube sidewall) 30 as compared to prior or current stent configurations, the intermediate layer 32 is preferably composed of a noble metal, most preferably platinum. Platinum has an atomic number ($Z=77$) almost three times that of steel, and therefore provides a highly radiopaque presence even though the overall dimension of this layer is very thin. To provide increased hardness, the platinum is preferably incorporated in an alloy with iridium, the latter in a percentage by overall weight in a range from about 2% to about 10%, preferably at or near the lower end of the range. The presence of iridium, which is of similar atomic number to platinum ($Z=78$), does not detract from the enhanced radiopacity of the intermediate layer 32. If a nitinol base layer is utilized rather than stainless steel or other medical implant-grade material, the iridium serves to improve the match between the physical characteristics of the nitinol layer and the intermediate layer.

The process by which the intermediate layer is applied preferably employs powder metallurgy. In addition to its other significant attributes, the surface tension and friction characteristic of the product to this point is improved over a stent having an ultra smooth surface. In the process, the particulate or powder metal is applied to the base layer surface and tightly bonded thereto, and built up to the desired layer thickness of high porosity by forming an interconnected multiplicity of the particles (microspheres), through application of heat. Suitable powder metallurgy processing for this material has been developed by Hittman Materials & Medical Components, Inc. of Columbia, Md.

The interstices 37 constituting the spaces or voids between the spherical platinum-iridium particles 33 are sufficiently sized and plentiful as a result of the formation of layer 32, to provide in overall effect a reservoir or repository for the infusion and retention of drugs which are beneficial or an aid to the use of the stent when implanted in a particular vessel or duct, such as in a coronary artery or other blood vessel. So the intermediate layer 32 provides not only the benefits of increased radiopacity of the stent, but also enables retention of drugs which may be released over time from the surface of the stent to enhance or inhibit certain functions.

For example, when the stent is intended for deployment at a selected site to support the inner lining of a coronary artery which has undergone an angioplasty procedure, to maintain the lumen thereof open, the outward facing surface of the stent and at least part of the edges of the openings adjacent thereto in the stent will ultimately be placed in contact and engagement with tissue of the inner lining of the artery wall. In contrast, the inward facing surface forms the lumen of the stent, and portions of the edges of the openings 16 (in the multi-layer final structure) will be contacted by blood flowing through the artery (and thereby, through the lumen of the implanted stent).

Therefore, the voids or pores 37 in the outward facing surface and adjacent edge surfaces of intermediate layer 32 are advantageously used in total as a repository for drugs formulated to inhibit inflammation or proliferation of tissue from trauma of the stent engagement or related mechanism—drugs such as dexamethasone or taxol, respectively, or both. The spaces between particles in the inward facing surface and adjacent edge surface of intermediate layer 32 are, on the other hand, suitable for use as a repository of drugs to inhibit thrombus or platelet formation attributable to presence of the stent in the bloodstream—drugs such as hirudin or iloprost, respectively, or both.

Before depositing or infusing any such selected drugs in the voids 37 between particles 33, however, a third layer or coating 40 may be and preferably is formed on the exposed surface(s) of the intermediate highly porous layer 32 of interconnected spherical platinum-iridium particles 33. This third or upper or outermost or superficial layer 40 is preferably composed of either iridium oxide (IROX) or titanium nitrate. Each of these materials is in the nature of a ceramic, i.e., is ceramic-like, and although either one of them is preferred for this embodiment, each is exemplary of a biocompatible layer that serves a primary purpose of avoiding tissue irritation and thrombus formation. This outermost layer may be deposited as an inert coating over the surface(s) of the underlying intermediate layer 32 by any known method, preferably to a thickness in the range from about 10 to 500 nanometers (nm), preferably nominally 200 nm.

Layer 40 need not and preferably does not fully coat all surfaces in the interstices of the porous intermediate layer 32, but need merely cover the more exposed surfaces of particles 33 of that underlying layer, so that when the completed stent is ultimately deployed it is this outer coating 40 that principally if not solely contacts the inner lining of the vessel and the blood flowing through the lumen of the vessel. As shown in FIG. 2, these are primarily the top surfaces of the uppermost spheres of intermediate layer 32. Hence, a sputtering process is adequate for providing the coating, and more desirable than a process that would include immersion of the stent as fabricated to this point in a solution of iridium where more extensive surface coverage is desired, in the case of iridium oxide. Here again, suitable processes have been developed and can be performed by Hittman Materials & Medical Components, Inc., for example. It is, of course, desirable that porous underlayer 32 be left with its voids 37 intact, i.e., not filled or substantially blocked with iridium oxide or titanium nitrate, so that the reservoir or repository remains available after application of coating 40, for infusion and retention of beneficial drugs.

The intermediate porous layer 32 also serves the purpose of providing, a suitable underlayer, along with base layer 30, to allow flexing of the stent over a vast number of cycles encountered in actual use without loss of the overlying iridium oxide or titanium nitrate coating from flaking, shedding or disintegration. After the outermost layer 40 is formed (or upon completion of the spherical platinum-iridium particulate layer 32, if only that layer is to be applied atop the base layer to essentially complete the stent), including such cleaning, rinsing and drying as is necessary to complete the process, the desired anti-inflammatory and/or anti-proliferation drugs are applied to enter the interstices of the porous medium constituting the outward facing surface and adjacent edges of openings of the stent. The desired anti-thrombotic and/or anti-platelet agents are applied to enter the interstices at the inward facing surface and adjacent edges of openings of the stent. By virtue of the very nature of this repository, the drugs or agents are, to an extent, time released therefrom to provide a primarily acute response to tissue trauma and clotting mechanisms.

The drug release response may be more carefully controlled by fabricating the-intermediate layer 32 in a manner to position the larger spheres of the platinum-iridium particulate matter 33 directly adjacent and bonded to the base layer surface, and increasingly smaller-sized particles as the uppermost region of the layer is approached, as represented in the showing of FIG. 2. This has the effect of increasing the size of the spaces 37 between particles at the bottom, and, thus, provides a larger reservoir or repository there, and of reducing the voids as the uppermost or outermost region is approached, whereby to reduce the spaces and reservoir volume in that region.

Additionally, or alternatively, the timed release of the beneficial drugs from the interstices of the porous layer 32 may be controlled by incorporating the drugs in a biodegradable carrier, preferably of a type described in the applicant's U.S. patent application Ser. No. 08/798,333. This carrier that contains the drugs or other applicable agents is represented at 43, by way of example, in the fragmentary exaggerated cross-section of FIG. 2. The time-controlled release in this case is attributable to the degradation or disintegration of the carrier itself, so that the drug or other agent remains captive within the carrier until it is dispensed or released, i.e., freed from its host, by progressive dissolution upon continuing diffusion of the carrier from the reservoir.

As an alternative to the infusion or incorporation of anti-proliferative or anti-inflammatory drugs into the reservoir along the outward facing porous structure of the intermediate layer, which is substantially retained and available after application of the non-filling, non-blocking final biocompatible coating, gene transfer may be used to inhibit the smooth muscle cell growth that leads to neointima and restenosis. In principle, a viral vector is used to transfer the desired information into the genome of the target cells. Viruses capable of such gene transfer are, for example, adenovirus and herpervirus, or fractions of the virus. By viral transfer, which is believed to occur by virtue of absorption and diffusion, part of the genetic information of interest is provided to the target cell. Such information can relate to several mechanisms of smooth muscle cell proliferation, with the aim of inhibiting restenosis which, if unchecked, could result in at least partial and perhaps complete blockage of the vessel's lumen, despite the presence of the deployed stent at the site.

One important technique involves blocking the proliferation stimulating factors such as cytoKines, n Fkappa b, platelet derived growth factors or other growth factors that originate from platelet deposition, thrombus formation, mechanical stress, or injury and inflammation. The applicant herein is currently investigating whether selective inducement of apotosis—or programmed cell death—may be achieved via the fas-ligand, which would enable a programmed intervention against overshooting cellular proliferation in a narrowly controlled region of the tissue.

The virus transfer is performed by incorporating the gene transfer agent—a viral vector or virus of the above-mentioned type that contains the viral genetic information desired to be transferred to the target cell(s)—into a biodegradable carrier, as at 43 of FIG. 2, for release from the reservoir into which it has been infused and dispensed by the process of biodegradation. Alternatively, the release to effect the gene transfer may be accomplished by release from a solution in the reservoir which contains liposomes as the viral vector.

The invention also contemplates the use of an intermediate high visibility layer which is completely solid, rather than porous, between the mechanical strength-and flexibility-providing layer which is the base material of the stent and the uppermost layer. Such a solid intermediate layer is also preferably composed of a noble metal, and most preferably a platinum-iridium alloy in which the percentage of iridium is relatively small, e.g., about 2%, and which provides excellent surface characteristics to promote a strong bonding or adherence of the final coating of iridium oxide or titanium nitrate. The intermediate layer here may be applied by a conventional electroplating, for example, or other suitable process, instead of a powder metallurgy technique, for example, by which a porous thickness can be provided. The final coating has a sufficiently rough exposed surface to assure some attachment of a carrier incorporating the aforementioned drugs or other agents therein, albeit not to an extent offered by the reservoir or repository provided by the porous layer of the preferred embodiment. Layer thicknesses are substantially the same as those for the preferred embodiment which utilizes a porous intermediate layer.

Figure 3:
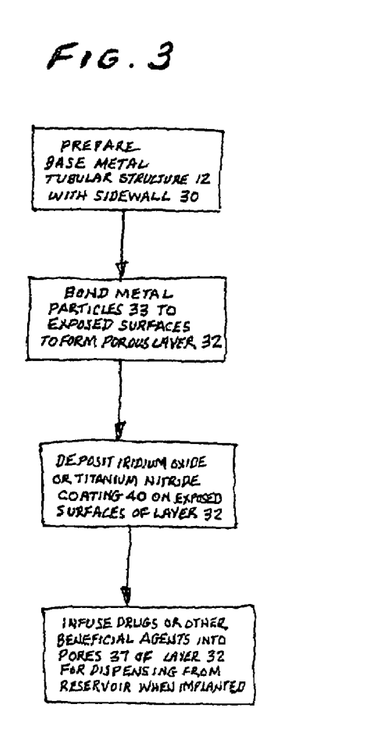
FIG. 3 is a flow chart diagram illustrating the steps of a basic process for fabricating a multi-layer stent of the type illustrated in FIGS. 1 and 2.

The basic process for fabricating a multi-layer stent of the type which has been described herein in conjunction with FIGS. 1 and 2 is illustrated in the flow chart of FIG. 3. First, the basic metal tubular structure 12 with sidewall 30 is prepared or implemented in any conventional manner. The example of starting with a tube having a solid sidewall has already been described earlier in this detailed description. Metal particles 33 are next bonded to the surface of the sidewall or basic layer 30 as well as to themselves to form intermediate porous layer 32, with sufficient voids between the particles therein to constitute a reservoir for retention of beneficial drugs, other agents, or virus vectors for gene transfer. An iridium oxide (or titanium nitrate) coating 40 is then applied to exposed of the porous layer 32 to provide a biocompatible surface for the overall basic stent. Finally, the drugs, agents and/or vectors to aid in overcoming undesired responses of the tissue and fluids of the body to intervention of the stent, are infused into the interstices 37 together with a biodegradable carrier to fill or partially fill the reservoir from which they are dispensed after the stent is implanted in the body.

Clinical studies required by protocols to obtain regulatory approval for marketing and use of medical devices in the United States generally mandate millions of cycles of flexation indicative of many years of deployment and usage of the stent, representative of the environment of the stent when implanted and in use in the human body.

Although a preferred embodiment and method of fabrication have been disclosed herein, it will be recognized by those of ordinary skill in the art to which the invention pertains, from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A method, comprising:
   providing a free-standing, expandable vascular metal stent including a first layer radially outward of at least one inner, metal-containing layer, the first layer comprising at least both: a) a ceramic material and b) a drug, contained within voids in said first layer, at least a substantial portion of said ceramic being positioned radially outward of said voids, wherein said ceramic material does not fully coat all outer surfaces of the first layer, and
   implanting the stent at the location of an angioplasty treatment.

2. The method of claim 1, wherein the ceramic material is selected from the group consisting of iridium oxide and titanium nitrate.

3. The method of claim 2, wherein the ceramic material is iridium oxide.

4. The method of claim 1, wherein the ceramic material has a thickness in the range from about 50 to 500 nanometers.

5. The method of claim 1, wherein the ceramic material does not block a release of the drug from the voids.

6. The method of claim 1, wherein the first layer has a thickness in the range from about to 4 to about 8 µm.

7. The method of claim 1, wherein the first layer comprises a noble metal.

8. The method of claim 7, wherein the first layer comprises an alloy of platinum and iridium.

9. The method of claim 1, wherein the at least one inner, metal-containing layer comprises a stainless steel or a nickel-titanium alloy.

10. The method of claim 1, wherein at least a substantial portion of the drug is positioned radially inward of the ceramic material.

11. A method, comprising:
    implanting a free-standing, expandable vascular metal stent at the location of an angioplasty treatment, the stent comprising:
    (a) a porous layer comprising voids;
    (b) a drug contained in the voids; and
    (c) a ceramic material on an outer surface of the porous layer, at least a substantial portion of the ceramic material being positioned radially outward of the voids, wherein the ceramic material does not fully coat all of the outer surface of the first layer.

12. The method of claim 11,
    wherein the porous layer comprises a noble metal; and
    wherein the ceramic material is selected from a group consisting of iridium oxide and titanium nitrate.

13. The method of claim 11, wherein the porous layer comprises an alloy of platinum and iridium.

14. The method of claim 11,
    wherein the porous layer has a thickness in the range from about 4 to about 8 µm; and
    wherein the ceramic material has a thickness in the range from about 50 to 500 nanometers.

15. The method of claim 11, wherein the ceramic material does not block a release of the drug from the voids.

16. The method of claim 11, further comprising a base metal layer, the porous layer being radially outward of the base metal layer.

17. The method of claim 16, wherein the base metal layer comprises a stainless steel or a nickel-titanium.

18. The method of claim 16, wherein the base metal layer has a thickness in the range from 60 to 80 µm.

19. The method of claim 11, wherein at least a substantial portion of the drug is positioned radially inward of the ceramic material.

20. A method, comprising:
    implanting a free-standing, expandable vascular metal stent at the location of an angioplasty treatment, the stent comprising:
    (a) a base metal layer, the base metal layer having a thickness in the range from 60 to 80 µm;
    (b) an intermediate porous layer being radially outward of the base metal layer, the intermediate porous layer having a thickness in the range from about 4 to about 8 µm, the intermediate porous layer comprising voids;
    (c) a drug contained in the voids; and
    (d) a ceramic material, at least a substantial portion of the ceramic material being positioned radially outward of the voids, wherein said ceramic material does not fully coat all outer surfaces of the intermediate porous layer.

21. The method of claim 20,
    wherein the base metal layer comprises a stainless steel or a nickel-titanium;
    wherein the intermediate porous layer comprises a noble metal; and
    wherein the ceramic material is selected from a group consisting of iridium oxide and titanium nitrate.

22. The method of claim 20, wherein the intermediate porous layer comprises an alloy of platinum and iridium.

23. The method of claim 20, wherein at least a substantial portion of the drug is positioned radially inward of the ceramic material.

* * * * *

UNITED STATES PATENT AND TRADEMARK OFFICE
CERTIFICATE OF CORRECTION

PATENT NO. : 7,713,297 B2  Page 1 of 1
APPLICATION NO. : 10/651562
DATED : May 11, 2010
INVENTOR(S) : Eckhard Alt It is certified that error appears in the above-identified patent and that said Letters Patent is hereby corrected as shown below:

Title Page; item (57);

First Page Column 2, line 6 (Abstract), please delete "substantial" and insert --substantially--, therefore.

Column 1, line 7, please delete "Dec. 15" and insert --Dec. 18,--, therefore.

Column 1, line 9, please delete "Apr. 1," and insert --Apr. 11,--, therefore.

Column 11, line 55 (Claim 6), after "about" please delete "to".

Signed and Sealed this

Twenty-eighth Day of September, 2010

David J. Kappos
*Director of the United States Patent and Trademark Office*